(12) United States Patent
Ba et al.

(10) Patent No.: US 11,226,323 B2
(45) Date of Patent: Jan. 18, 2022

(54) AIR-POLLUTION EMISSION SOURCE MONITORING

(71) Applicant: International Business Machines Corporation, Armonk, NY (US)

(72) Inventors: Yu Tao Ba, Beijing (CN); Gang Zhou, Beijing (CN); Lingyun Wang, Beijing (CN); Wei Zhao, Beijing (CN); Ming Xie, Beijing (CN); Ke Xu Zou, Beijing (CN); Xiao Guang Rui, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 288 days.

(21) Appl. No.: 15/964,634

(22) Filed: Apr. 27, 2018

(65) Prior Publication Data
US 2019/0331652 A1 Oct. 31, 2019

(51) Int. Cl.
*G01N 33/00* (2006.01)

(52) U.S. Cl.
CPC ..... *G01N 33/0075* (2013.01); *G01N 33/0036* (2013.01); *G01N 33/0062* (2013.01)

(58) Field of Classification Search
CPC .......... G01N 33/0075; G01N 33/0036; G01N 33/0062
See application file for complete search history.

(56) References Cited

U.S. PATENT DOCUMENTS 5,831,876 A * 11/1998 Orr .................. G06T 17/05
703/6

7,834,754 B2 * 11/2010 Kulesz .................. G08B 21/12
340/506

(Continued)

FOREIGN PATENT DOCUMENTS

| CN | 102184284 A | * | 9/2011 |
| CN | 103455012 A | | 12/2013 |
| WO | 2017093728 A1 | | 6/2017 |

OTHER PUBLICATIONS

Alain, CeLisse ,Optimal Cross-Validation In density estimation with L2-Loss,The Annals of Statistics , 2014, vol. 42, No. 5, (Year: 2014).*

(Continued)

*Primary Examiner* — Catherine T. Rastovski
*Assistant Examiner* — Aeysha N Sultana
(74) *Attorney, Agent, or Firm* — Jorge R. Maranto

(57) ABSTRACT

A computer implemented method, computer system, and computer program product are provided for air-pollution emission source monitoring. To determine the air-pollution emission of a monitored area, location data and air pollution data are taken from sensor stations positioned along a boundary of the monitored area. The macroscale atmospheric data of a region, where the monitored area is located, is also received. A boundary pollutant distribution can be estimated based on the location data and the air pollution data. Horizontal diffusion and vertical diffusion of the monitored area can be estimated based on the boundary pollutant distribution and the macroscale atmospheric data. To determine an accurate amount of pollution contribution caused by a monitored area, a calculation based on the boundary pollutant distribution, the horizontal diffusion, and the vertical diffusion can be used.

18 Claims, 11 Drawing Sheets

(56) References Cited

U.S. PATENT DOCUMENTS

| | | | |
|---|---|---|---|
| 9,599,529 B1* | 3/2017 | Steele | G01N 25/20 |
| 2009/0309744 A1* | 12/2009 | Fu | G08B 27/006 |
| | | | 340/632 |
| 2011/0251800 A1* | 10/2011 | Wilkins | G01N 21/33 |
| | | | 702/24 |
| 2012/0166022 A1 | 6/2012 | Kwon et al. | |
| 2012/0297028 A1 | 11/2012 | Das et al. | |
| 2013/0110400 A1* | 5/2013 | Moshe | G01W 1/00 |
| | | | 702/3 |
| 2014/0032175 A1* | 1/2014 | Agrawal | H04L 67/12 |
| | | | 702/189 |
| 2016/0290979 A1 | 10/2016 | Cogill et al. | |
| 2017/0038088 A1* | 2/2017 | Korber | F24F 3/16 |
| 2017/0140282 A1* | 5/2017 | Bai | G06N 7/00 |
| 2017/0227509 A1* | 8/2017 | Chang | G01N 33/0036 |
| 2018/0073759 A1* | 3/2018 | Zhang | G05B 17/02 |
| 2018/0080891 A1* | 3/2018 | Potyrailo | G01N 33/0036 |
| 2018/0202824 A1* | 7/2018 | Borrel | G01C 21/32 |
| 2019/0113445 A1* | 4/2019 | Zhang | G01N 33/0031 |
| 2021/0278387 A1* | 9/2021 | Bistany | G01N 33/0031 |

OTHER PUBLICATIONS

Heimann et al, "Source attribution of air pollution by spatial separation using high spatial density networks of low cos air quality sensors",2015 (Year: 2015).*

F.Tavakoli and J.S.Olfert,An Instrument for the Classification of Aerosols by Particle Relaxation Time:, Sep. 27, 2012 (Year: 2012).*

Alain, CeLisse .Optimal Cross-Validation In density estimation with L2-Loss,The Annals of Statistics , 2014, vol. 42, No. 5, (Year: 2014) (Year: 2014).*

Heimann et al, "Source attribution of air pollution by spatial separation using high spatial density networks of low cos air quality sensors",2015 (Year: 2015) (Year: 2015).*

F.Tavakoli and J.S.Olfert.An Instrument for the Classification of Aerosols by Particle Relaxation Time:, Sep. 27, 2012 (Year: 2012) (Year: 2012).*

Mareddy Impacts on air environment, Dec. 2017, In book—Environmental Impact Assessment (Year: 2017).*

Alain, Ceüsse Optimal Cross-Validation In density estimation with L2-Loss.The Annals of Statistics , 2014, vol. 42. No. 5, (Year 2014).*

Heimann et al. "Source attribution of air pollution by spatial separation using high spatial density networks of low cos air quality sensors".2015.*

F.Tavakoli and J.S.OlfertAn Instrument for the Classification of Aerosols by Particle Relaxation Time:, Sep. 27, 2012.*

"Air Monitoring, Measuring, and Emissions Research," EPA, printed Oct. 4, 2017, pp. 1-6. https://www.epa.gov/air-research/air-monitoring-measuring-and-emissions-research.

Mell et al., "The NIST Definition of Cloud Computing: Recommendations of the National Institute of Standards and Technology," Special Publication 800-145, Sep. 2011, 7 pages, National Institute of Standards and Technology, Gaithersburg, MD.

* cited by examiner

AIR-POLLUTION EMISSION SOURCE MONITORING

BACKGROUND

Embodiments of the disclosure relate to methods and systems that monitor sources of environmental pollution. More specifically, embodiments of the disclosure relate to air pollution source monitoring systems and methods.

Pollution is the introduction of substances or contaminants into the environment that have harmful or adverse effects. Over the centuries, civilizations have become more developed and industrialized. Due to advancements in industry and technology, harsh changes in the environment have occurred, and in particular, to the quality of the air in the environment. Traditionally, sources of pollution are said to be from stationary locations such as industrial factories, power plants, and sewage facilities. However, other sources of pollution arise in areas that have smaller individual sources, but when aggregated, contribute largely to the overall pollution in the environment. These sources can range from large cities, farms with livestock, and mobile vehicles such as cars, trucks, buses, and motorcycles.

Pollutants from the above sources may include ozone, nitrogen dioxide, Sulphur dioxide, carbon monoxide, and lead. While dispersed in the environment, these pollutants are broken down into particulate matter that the industry has denoted as $PM_{2.5}$ and $PM_{10}$. $PM_{10}$ is particulate matter 10 micrometers or less in diameter and $PM_{2.5}$ is particulate matter 2.5 micrometers or less in diameter. The pollutants are traditionally monitored by using emission source monitoring stations that are positioned near the pollution emitting source.

However, traditional methods of emission source monitoring are not an effective tool to accurately detect the true amount of particulate matter pollution that is being emitted into the environment. Areas that have multiple source points of emissions like vehicles, roadways, and livestock are difficult to accurately monitor. Also, single point stationary source monitoring can be influenced by weather conditions that skew the readings. In some developing countries, pollution emitting exhaust ports are changed and are not monitored, or the corporations conducting internal monitoring falsify the emission recording logs.

SUMMARY

The following presents a simplified summary of the disclosure in order to provide a basic understanding to the reader. This summary is not an extensive overview of the disclosure and it does not identify key/critical elements of the disclosure or delineate the scope of the disclosure. Its sole purpose is to present some concepts disclosed herein in a simplified form as a prelude to the more detailed description that is presented later.

Embodiments of the disclosure are directed to methods and systems that satisfy the need to accurately monitor air pollution that is being emitted over an area of land. To monitor air pollution, one embodiment may be a computer-implemented method comprising the steps of obtaining location and air pollution data from sensors at stations that are deployed along a boundary of a monitored area. The step of obtaining macroscale atmospheric data of a region, wherein the monitored area is contained within the region. The step of estimating a boundary pollutant distribution according to the location data and the air pollution data. The step of estimating horizontal and vertical diffusion within the monitored area according to the boundary pollutant distribution and the macroscale atmospheric data. Finally, the step of calculating an accurate amount of pollution contribution, within the monitored area, according to the boundary pollutant distribution and the estimations of the horizontal and vertical diffusion. To obtain the estimations and calculations, the steps can be carried out by one or more processors.

According to another embodiment, there is a computer system comprising of at least one processor and a computer-readable memory source coupled to the processor. The memory source comprises of instructions, that when executed by the processor, perform a method. The method comprising the steps of obtaining location and air pollution data from sensors at stations that are deployed along the boundary of a monitored area. The step of obtaining macroscale atmospheric data of a region, wherein the monitored area is contained within the region. The step of estimating a boundary pollutant distribution according to the location data and the air pollution data. The step of estimating horizontal and vertical diffusion within the monitored according to the boundary pollutant distribution and the macroscale atmospheric data. Finally, the step of calculating an accurate amount of pollution contribution, within the monitored area, according to the boundary pollutant distribution and the estimations of the horizontal and vertical diffusion According to another embodiment, a computer readable storage medium having computer readable instructions that when executed by a computer having at least one processor cause the computer to obtain location data and air pollution data from sensors at stations deployed along a boundary of a monitored area. The computer obtains macroscale atmospheric data of a region, wherein the monitored area is contained within the region. The computer estimates a boundary pollutant distribution according to the location data and the air pollution data. The computer estimates horizontal and vertical diffusion of the monitored according to the distribution of boundary pollutant and the macroscale atmospheric data. Finally, the computer calculates an accurate amount of pollution contribution, within the monitored area, according to the boundary pollutant distribution and the estimations of the horizontal and vertical diffusion.

BRIEF DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

Figure 1:
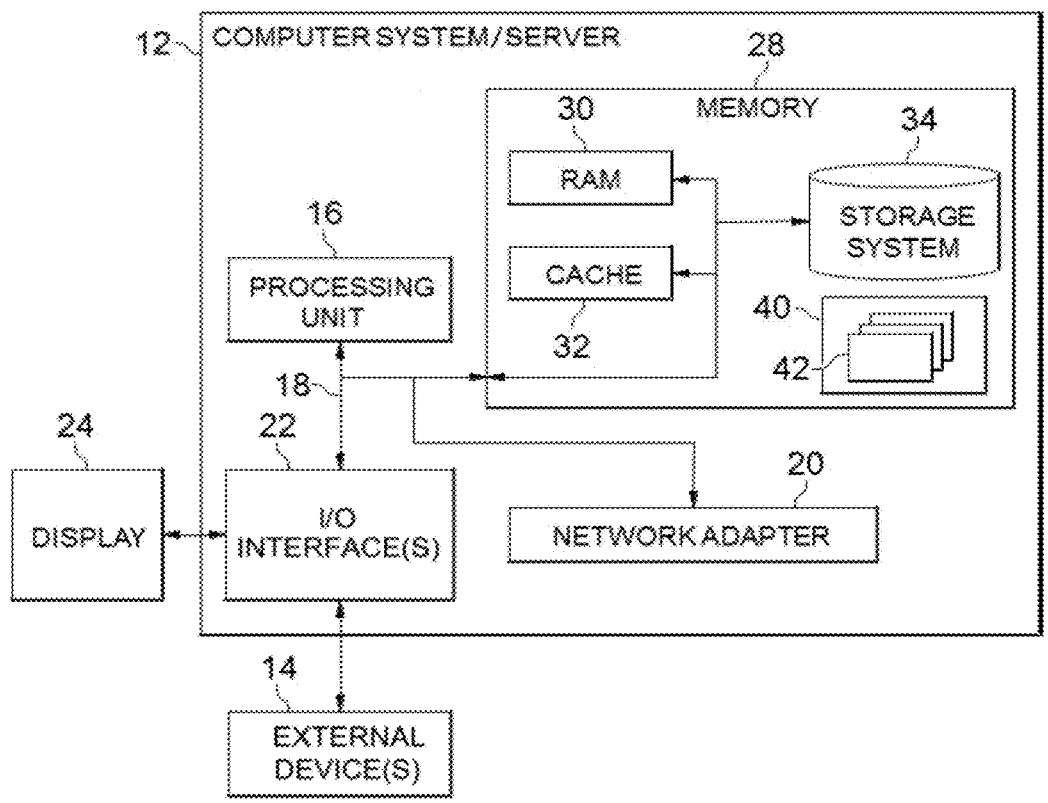
FIG. 1 depicts a cloud computing node according to one illustrative embodiment.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 2:
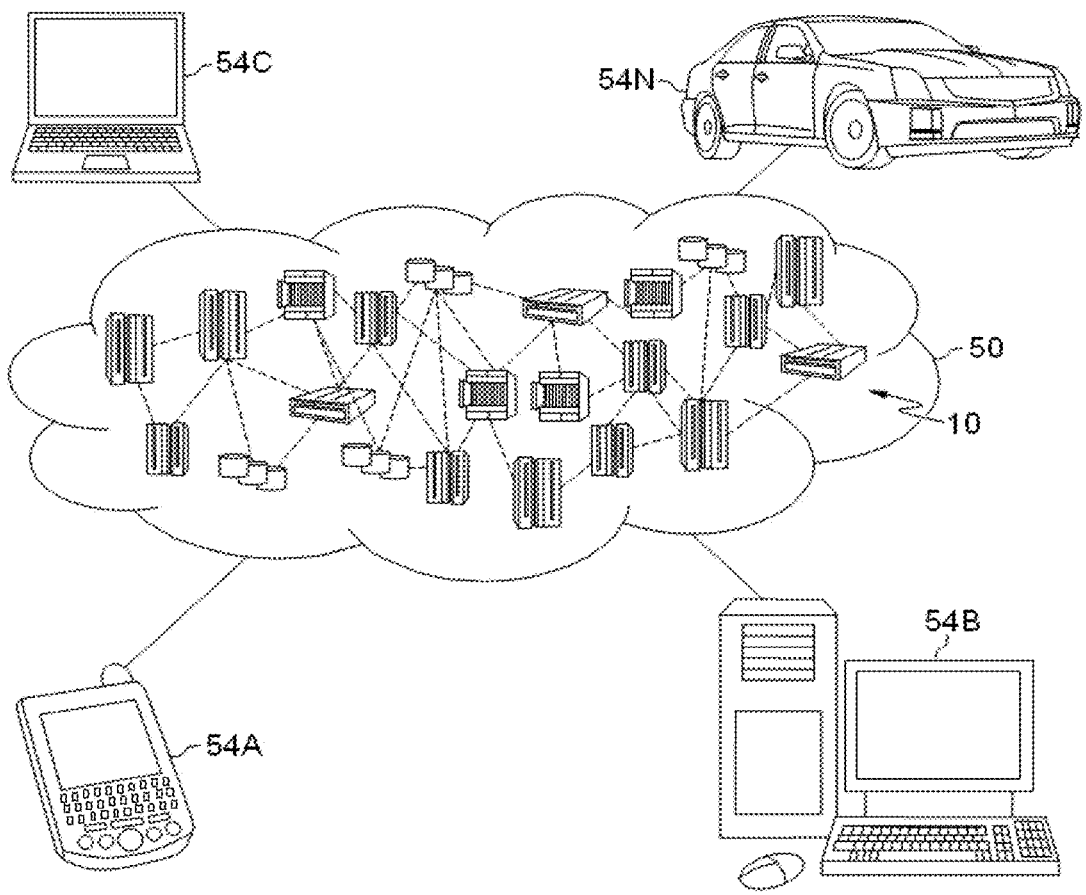
FIG. 2 depicts a cloud computing environment according to one illustrative embodiment.

Referring now to FIG. 1, a schematic of an example of a computer system/server 12 (e.g., a cloud computing node) is shown. Cloud computing node 10 of FIG. 2 is only one example of a suitable cloud computing node and is not intended to suggest any limitation as to the scope of use or functionality of embodiments of the disclosure described herein. Regardless, cloud computing node 10 is capable of being implemented and/or performing any of the functionality set forth hereinabove.

In cloud computing node 10 there is a computer system/server 12 or a portable electronic device such as a communication device, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random-access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the disclosure as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via input/output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. Although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
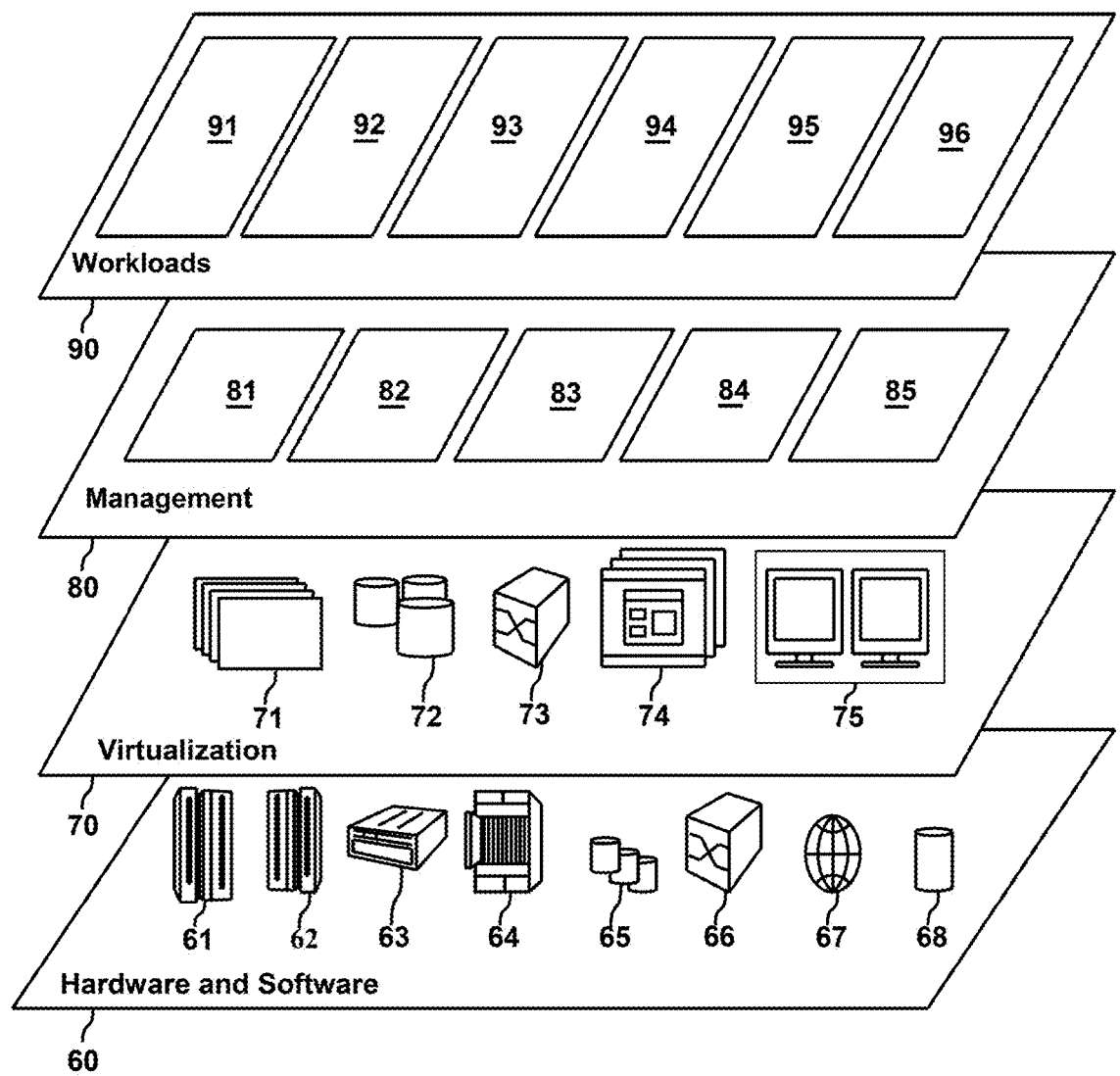
FIG. 3 depicts abstraction model layers according to one illustrative embodiment.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the disclosure are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and air-pollution emission source monitoring 96.

Figure 4:
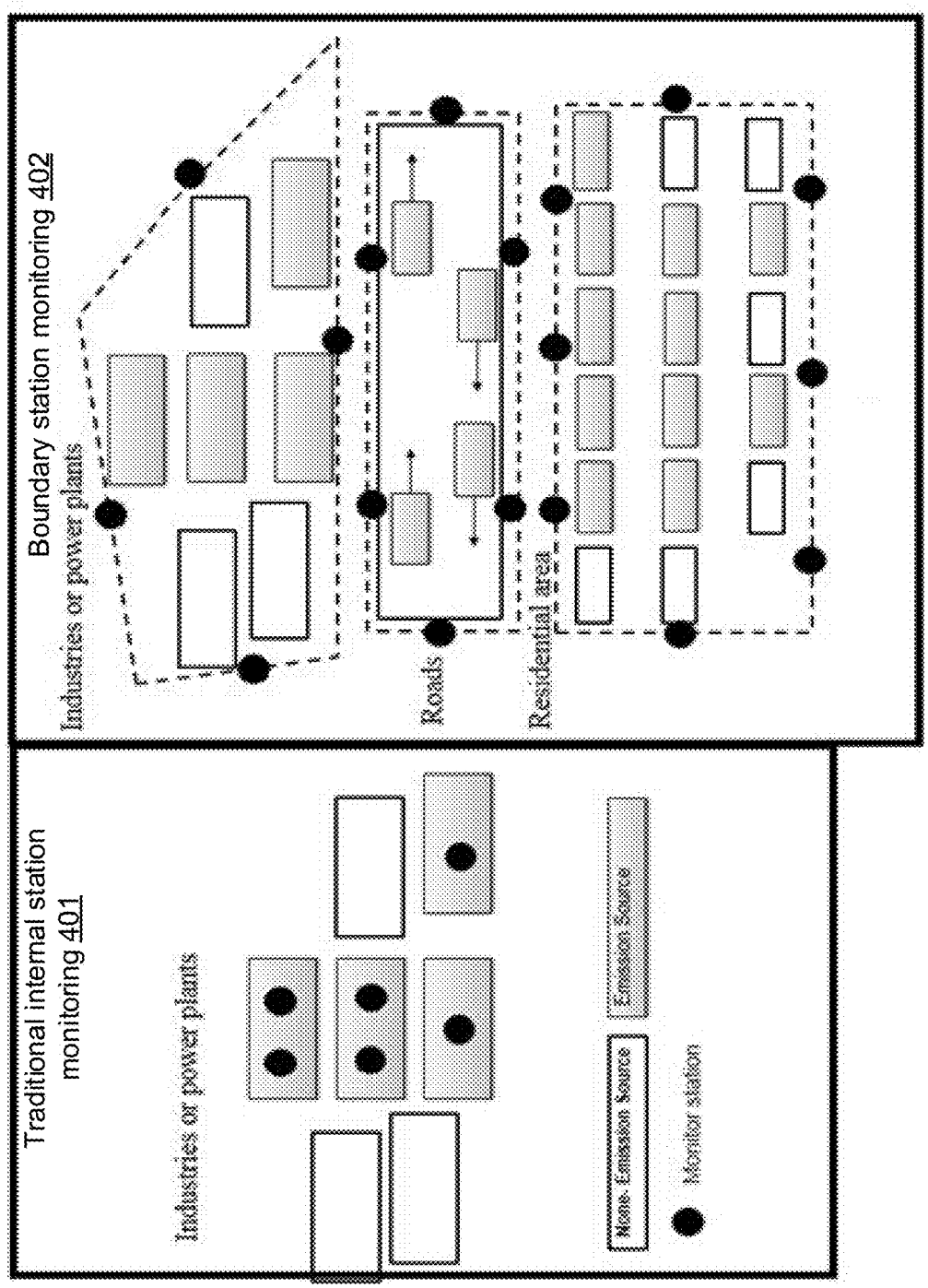
FIG. 4 illustrates the comparison between the traditional internal station monitoring and boundary station monitoring according to one illustrative embodiment.

At least one sensor, used for measuring at least one parameter of air-pollution emission, is typically installed within a monitoring station. At least one sensor is needed for each station. The number of sensors needed is based on the requirements of the station. In other words, each station may be installed with at least one sensor where at least one parameter is needed to be measured. To overcome the challenges described above, stations may be deployed differently according to various embodiments. This contrasts with a traditional internal monitoring model where the monitoring stations, with pollutant sensors, are only deployed inside or nearby the exhaust ports, such as chimneys, within a monitored area. In one embodiment, stations, installed with sensors, are deployed along the boundary of a monitored area such as an industry, a power plant, a busy road, or a large residential area. To illustrate, FIG. 4 shows the comparison between traditional internal station monitoring and boundary station monitoring according to one illustrative embodiment. In traditional internal station monitoring 401, stations are deployed inside or nearby the exhaust ports, such as chimneys, in the monitored area. In boundary station monitoring 402, according to one illustrative embodiment, stations are deployed along the boundary of the monitored area. At least one sensor, that measures air pollutants, is installed at each station around the boundary. The number of stations along the monitored area's boundary can be determined by the size and type of area based on the following principle:

(a) The baseline number of stations to be deployed around an area can be calculated as follows:

$$N_{baseline}=2*(\text{size of the monitored area})^{1/2} \quad \text{(Equation 1)}$$

Where $N_{baseline}$ is the baseline number of stations needed for a given area. For example, at least 4 stations are needed for an area of 4 km$^2$, and at least 8 stations for an area of 16 km$^2$.
(b) If there are more emission sources in an area compared to areas with a typical number of concentrated emission sources, or if the emission sources are moving, the number of stations along the boundary should increase accordingly. For example, a busy road may have emission sources, like vehicles, that are moving. Due to the moving emission sources, the monitored area encompassing a busy road may need more stations than an industry or a power plant of a similar area. The emission sources of a residential area are often more scattered than other monitored areas, so the boundary of residential area may also need more stations. For the above-mentioned cases, the number of stations needed can be calculated by multiplying the baseline number with a coefficient k. For example, $$N=k*N_{baseline}=k*2*(\text{size of the monitored area})^{1/2}, k>1, \text{ as an example, } k=1.2 \quad \text{(Equation 2)}$$

Once the number of stations needed for a monitored area is determined, the position of each station, that has a monitoring sensor, can be obtained. This can be accomplished by utilizing GPS in real-time during the first installment as $x_i$=(Longitude, Latitude), in which i is a natural number and stands for the i$^{th}$ station.

The sensors that are installed at the stations can be obtained by typical means. These sensors can vary in type, where the sensors are capable of measuring one or more parameters of pollution data as shown in Table 1 below.

TABLE 1

| Parameters | unit |
|---|---|
| PM$_{2.5}$ or concentration of other air pollutants | ug/m3 |
| surface wind | m/s and direction |
| temperature | ☐ |
| pressure | Pa |
| GPS longitude/latitude (optional) | Degrees (°) |

Figure 5:
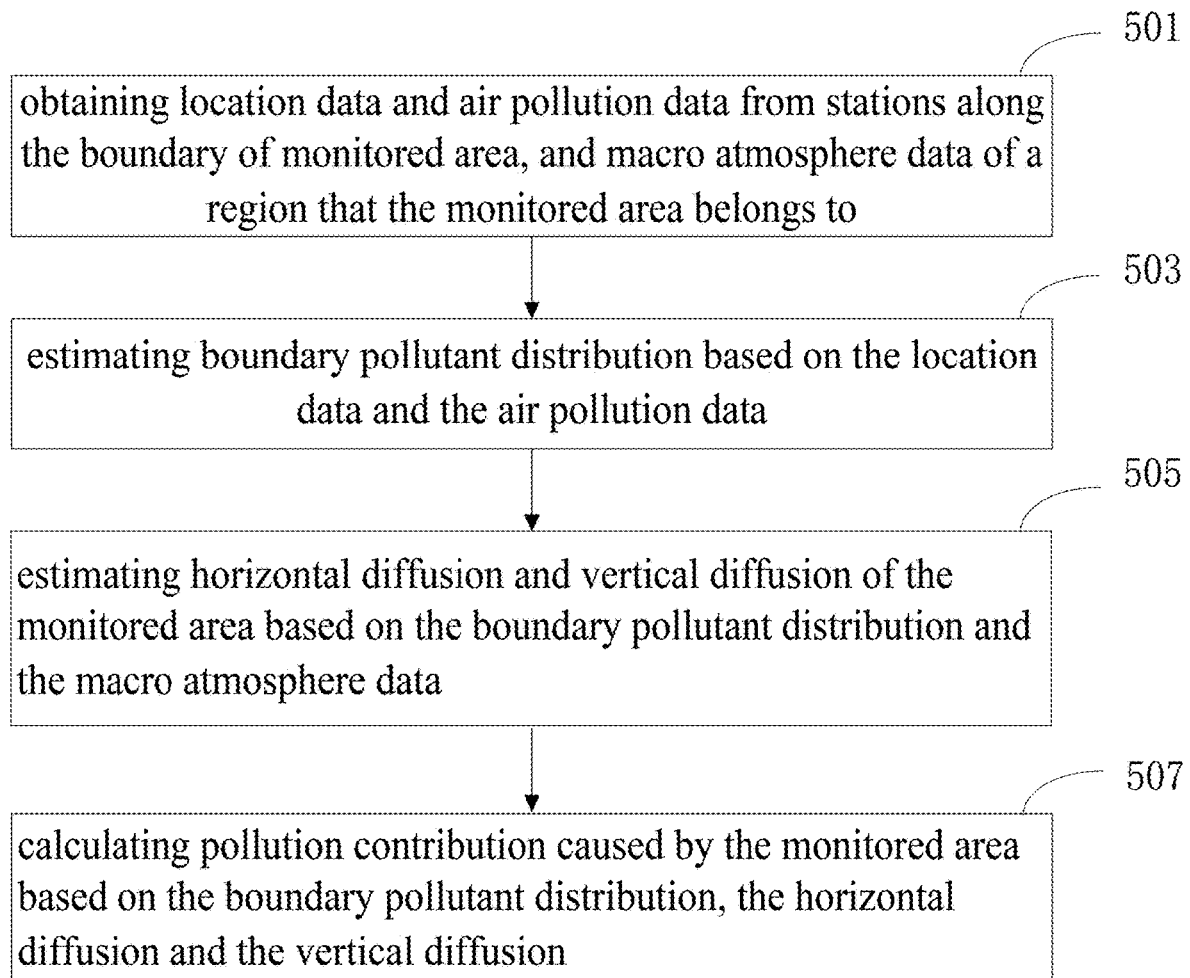
FIG. 5 is a flow diagram illustrating an exemplary method of air-pollution emission source monitoring according to one illustrative embodiment.

FIG. 5 is a flow diagram illustrating a process of air-pollution emission source monitoring according to one illustrative embodiment. As illustrated in step 501, location and air pollution data is obtained from stations positioned along the boundary of a monitored area. Macroscale atmospheric data of a region, where the monitored area is within, is also obtained. The macroscale atmospheric data of the region, where the monitored area is within, can be obtained from readily available governmental records or other public organizations. Table 2, shown below, provides an example of macroscale atmospheric data parameters. Typically, the region is much larger than the monitored area. Thus, the macroscale atmospheric data may deviate from the sensor data because the macroscale atmospheric data is calculated by taking the average value of the larger region.

TABLE 2

| Parameters of macro measures | unit |
|---|---|
| surface wind | m/s and direction |
| vertical wind | m/s and direction |
| Temperature | ° C. |
| Pressure | Pa |

Figure 6:
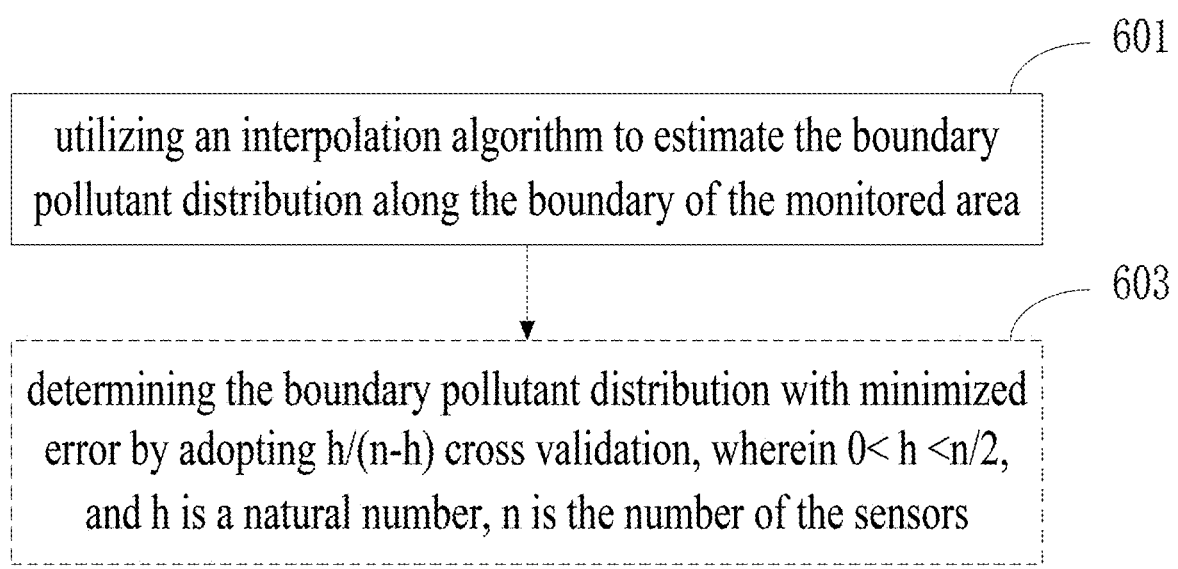
FIG. 6 is a flow diagram of how the boundary pollutant distribution is estimated according to one illustrative embodiment.

As illustrated at step 503, the boundary pollutant distribution is estimated utilizing the location data and the air pollution data. The boundary pollutant distribution measures the distribution of pollutant along the boundary of the monitored area. FIG. 6 is a flow diagram illustrating a process of how the boundary pollutant distribution is estimated according to one illustrative embodiment. As illustrated at step 601, the boundary pollutant distribution is estimated by utilizing an interpolation algorithm along the boundary of the monitored area. The surface of pollutant concentration within the monitored area can be estimated by a two-dimensional interpolation F=f̂(x,y,t), where y indicates the pollutant concentration of any position x within the monitored area at any time t, and F=f̂(x,y,t) can be estimated as equation (3) as below.

$$F = \hat{f}(x, y, t) = \begin{cases} \dfrac{\sum_i d(\{x_i, y_i, t_i\}, \{x, y, t\})^m \cdot f(x_i, y_i, t_i)}{\sum_i d(\{x_i, y_i, t_i\}, \{x, y, t\})^m}, & \text{If } d(\{x_i, y_i, t_i\}, \{x, y, t\}) \neq 0 \text{ for all } i \\ f(x_i, y_i, t_i), & \text{If } d(\{x_i, y_i, t_i\}, \{x, y, t\}) = 0 \text{ for certain } i \end{cases}$$

(Equation 3)

The parameter m is the argument of interpolation (m may be optimized through means encompassed within another embodiment. An example of such embodiment is discussed later.) The parameter $y_i$ indicates the air pollutant concentration measured by the sensors (such as $PM_{2.5}$). The parameter $x_i$ indicates the location of station i where at least one sensor is installed and where $x_i$=(Longitude, Latitude). The parameter $t_i$ is the amount of time where at least one sensor at station i conducted the measurements. The parameter $d(\{x_i, y_i, t_i\}, \{x,y,t\})$ represents the regularized Mahalanobis distance from {xi, yi} to {x,y} at time t. If $t_i$ is not equal to t, t can be selected as the nearest $t_i$.

Figure 7:
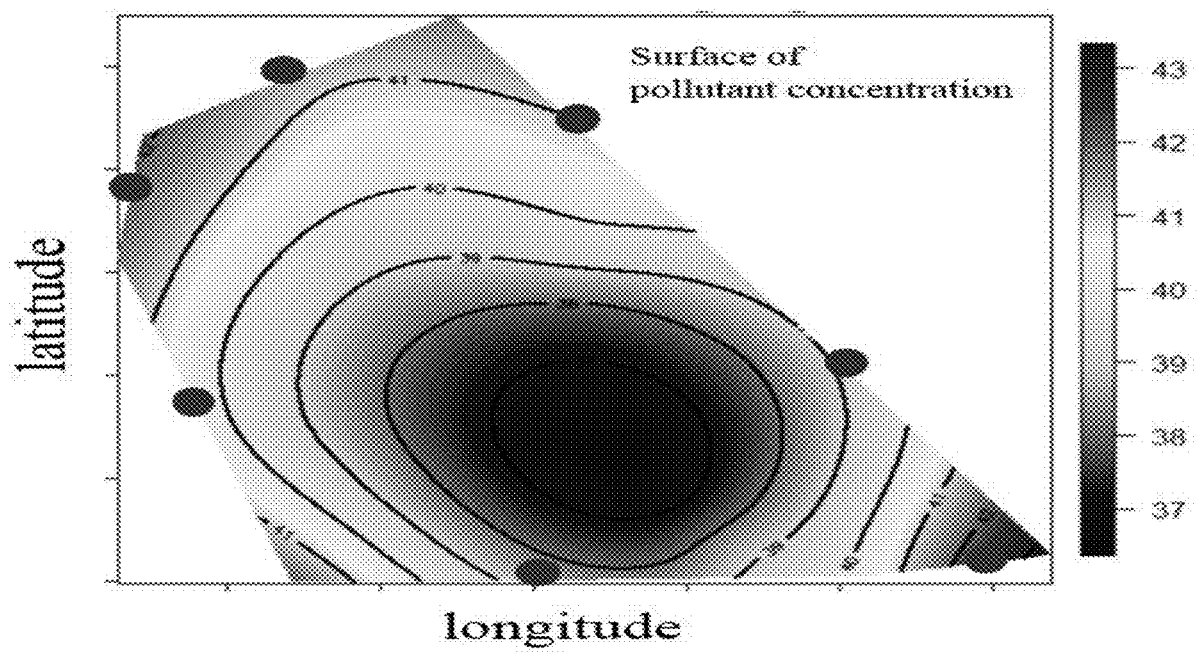
FIG. 7 illustrates the surface of pollutant concentration of the monitored area estimated based on the location data and the air pollution data according to one illustrative embodiment.

FIG. 7 shows the surface of pollutant concentration within the monitored area. Utilizing equation (3), the pollutant concentration is estimated by applying the location data and the air pollution data to the equation. The solid curves show the contours of estimated pollutant concentration. The surface variations may occur when m differs. This occurs when there is an optimization of m as discussed below.

In another embodiment, the surface of pollutant concentration in FIG. 7 can be optimized to reduce error between the estimation and the observation of pollutant concentration. As illustrated in step 603, to minimize error, the pollutant distribution can be estimated by adopting 1/(n−1) cross validation, where n is the number of the stations. Each time the pollution data, of (n−1) stations, is selected for interpolation, it is necessary to obtain the pollutant distribution that is based off equation (3), as well as one station must be selected to assess the error of interpolation. The error measurements can be calculated by equation (4) as below:

$$E = \frac{1}{n}\sum E_j = \frac{1}{n}\sum \{\hat{f}(x_j, y_j, t) - y_j\}$$

(Equation 4)

in which j is the unique identifying number of the station used for error estimation.

Figure 8:
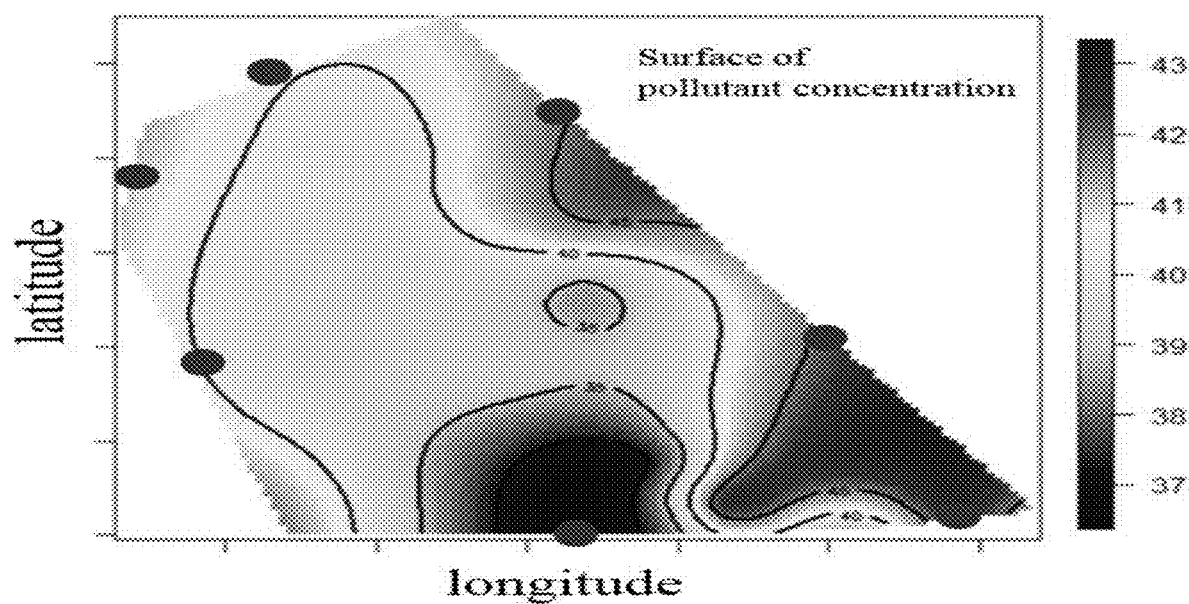
FIG. 8 illustrates the optimized surface of pollutant concentration of the monitored area according to one illustrative embodiment.

FIG. 8 shows the optimized the surface of pollutant concentration where the interpolation argument value m, with the smallest amount of error, is chosen to optimize the surface of pollutant concentration. The boundary pollutant distribution can be obtained when the surface of pollutant concentration is estimated by clipping the edges of surface pollutant concentration.

The two-dimensional interpolation algorithm, discussed above, is only an example. One station taken as the validation station is an example as well. However, two or more validation sensors can be utilized. For example, they can adopt h/(n−h) cross validation, wherein 0<h<n/2, and h is a natural number. Other kinds of interpolation and validation methods can also be utilized. Thus, the choice of interpolation or validation methods, by a person skilled in this art, does not adversely limit the scope of the disclosure.

Figure 9:
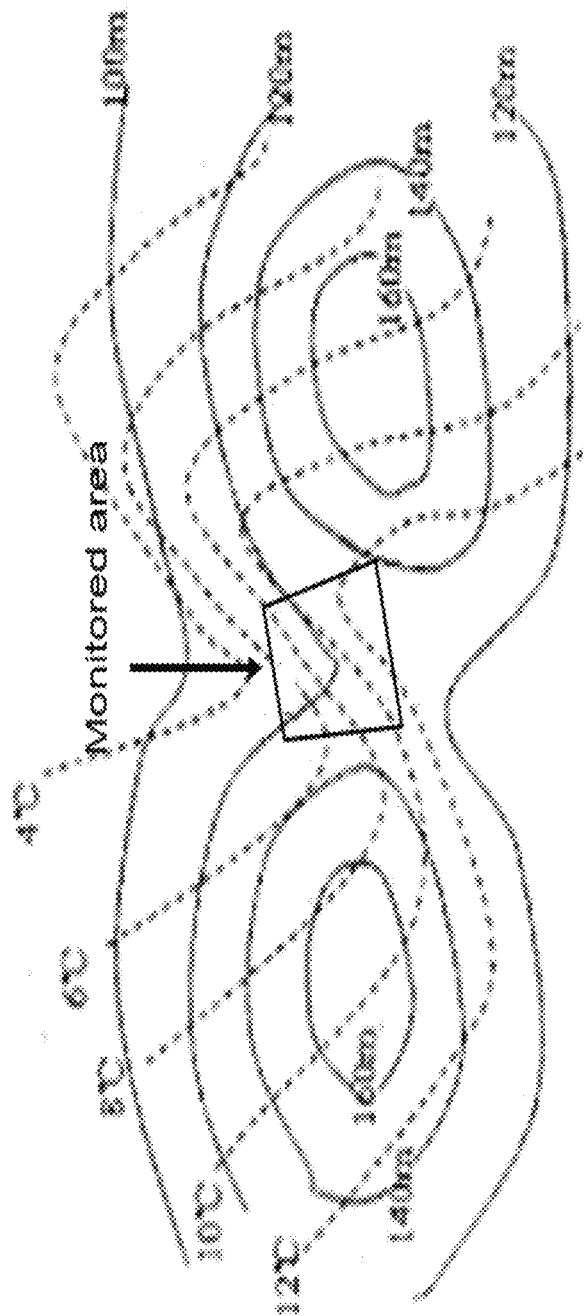
FIG. 9 illustrates the relationship between the region of macroscale atmospheric data and the monitored area according to one illustrative embodiment.

As illustrated in step 505, the estimations of horizontal diffusion and vertical diffusion, within the monitored area, are estimated separately by utilizing the boundary pollutant distribution, the air pollution data, and the macroscale atmospheric data. Also, to estimate the horizontal diffusion and vertical diffusion, surface wind and vertical wind readings, that are within the area, are needed. Typically, the macroscale atmospheric data from Table 2 is utilized to estimate the horizontal and vertical structure of the atmosphere in the monitored area. FIG. 9 illustrates the relationship between the region of macroscale atmosphere and the monitored area. The solid contour lines show the temperature distribution, and the dashed contour lines show the height of 950 hPa of atmospheric pressure. Atmosphere fusion technology can be utilized to combine the macroscale atmospheric data and the air pollution data, taken from the sensors (surface wind, temperature, pressure), to model the pollutant fusion in the monitored area and decrease the error from macroscale atmospheric data. Atmosphere fusion/assimilation technologies are well-known in prior arts and will not be explained in greater detail.

Figure 10:
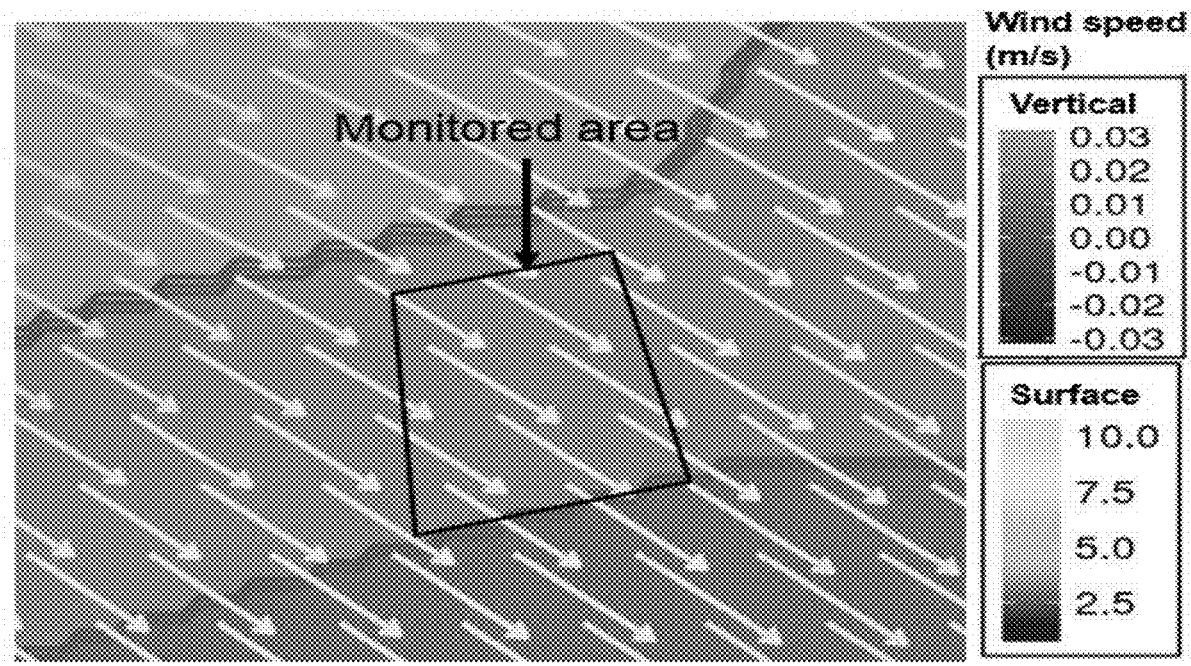
FIG. 10 illustrates the fusion result according to one illustrative embodiment.

FIG. 10 illustrates an example of a result of fusion result according to one embodiment. The arrows show the direction and strength of the surface wind. The filled colors, displayed in grey scale, show the direction and strength of the vertical wind. The parameters of combined pollutant fusion can be displayed as shown in Table 3.

TABLE 3

| Parameters of combined pollutant fusion | unit |
|---|---|
| surface wind | m/s and direction |
| vertical wind | m/s and direction |

Figure 11:
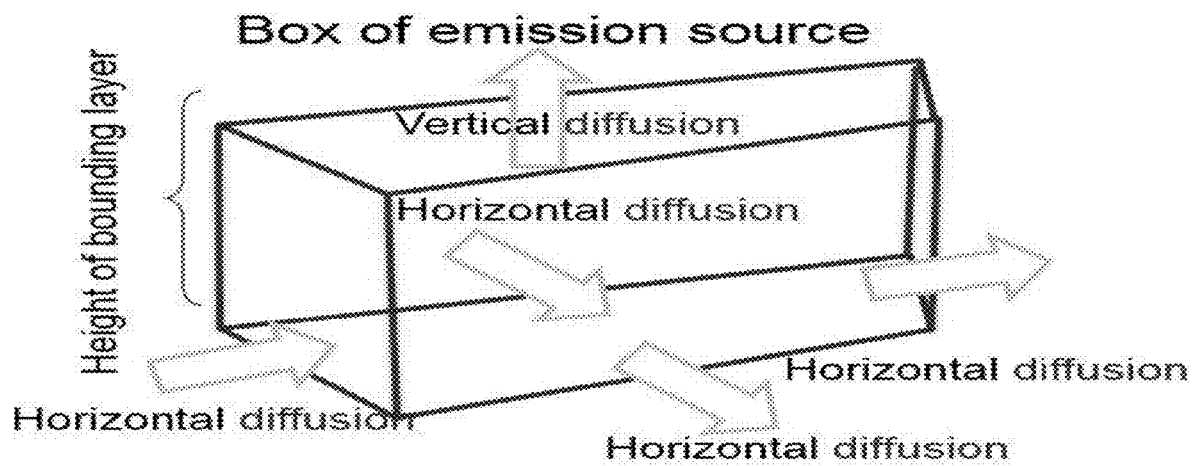
FIG. 11 illustrates the box model built for the monitored area according to one illustrative embodiment.

To estimate the horizontal diffusion and the vertical diffusion, a box model can be utilized for the monitored area. FIG. 11 illustrates a box model, in which the base of the box correlates to the monitored area. The height of the box correlates with the height of the atmospheric surface layer. For example, a person skilled in this art can determine an atmospheric surface layer to be 200 meters. Pollutant particles can be any particles that a sensor can monitor. For example, pollutant particles can be ozone, Sulphur dioxide, nitrogen dioxide, and other particulates that are broken down into coarse particulate matter. Hereinafter, embodiments will be described with the pollutant particles rated at $PM_{2.5}$. However, the description below is only for the purpose of illustration. Thus, the use of $PM_{2.5}$ will not adversely limit the scope of the disclosure. In one embodiment, the average mass concentration of $PM_{2.5}$ in the box can be calculated along the boundary of the monitored area using equation (5) as shown:

$$C_{PM2.5}(t) = \oint \hat{f}(x,y,t)dx / \oint xdx$$

(Equation 5)

in which t is a time variable, $C_{PM2.5}(t)$ represents the $PM_{2.5}$ concentration of the box at time t.

The horizontal diffusion $D_{horizontal}(t)$ and vertical diffusion $D_{vertical}(t)$ of the monitored area can be estimated as equation (6) and (7) as shown:

$$D_{horizontal}(t) = \{\oint f(x,y,t) \cdot \vec{w}_{surface} dx\} \cdot h \quad \text{(Equation 6)}$$

$$D_{vertical}(t) = \{\iint f(x,y,t) \cdot \vec{w}_{surface} dx\} \cdot A \quad \text{(Equation 7)}$$

in which $\vec{w}_{surface}$ indicates the surface wind and $\vec{w}_{vertical}$ indicates the vertical wind of Table 3. The h indicates the height of box, and A indicates the area size of the base of the box (i.e., area size of the monitored area). When the horizontal diffusion >0, the pollutant diffusion is diffused in a horizontal direction from the inside of the box, to the outside of box. When the vertical diffusion >0, the pollutant diffusion is diffused in a vertical direction from inside the box to the outside of the box. If the horizontal diffusion <0 or vertical diffusion <0, the pollutant diffusion occurs from the outside of the box to the inside of the box.

As illustrated at step 507, the pollution contribution caused by the monitored area is calculated utilizing the boundary pollutant distribution, the horizontal diffusion, and the vertical diffusion. The average of the $PM_{2.5}$ concentration in the box can be calculated as shown above. The changing rate of the pollutant concentration in the monitored area $\Delta T(t)$ can calculated based on the total pollutant concentration, which is the total $PM_{2.5}$ concentration in the box, by utilizing equation (8) as shown:

$$\Delta T(t) = \{C(t+\Delta t) - C(t)\} \cdot h \cdot A \quad \text{(Equation 8)}$$

in which $\Delta T(t)$ is the changing rate of the total $PM_{2.5}$ concentration in the box at time t. The change rate of the pollutant concentration is calculated based on the horizontal diffusion and the vertical diffusion as the equation (9) as shown:

$$\Delta T(t)_{calibration} = \Delta T(t) + \int_{t}^{t+\Delta t} \{D_{horizontal}(t) + D_{vertical}(t)\} dt \quad \text{(Equation 9)}$$

$\Delta T(t)_{calibration}$ is the calibrated changing rate of the total $PM_{2.5}$ concentration in the box. The pollution contribution caused by emission source in the monitored area $\Delta C_E(t)$ can be calculated based on the $\Delta T(t)_{calibration}$ as equation (10) shows:

$$\Delta C_z(t) = \Delta T(t)_{calibration} / (h \cdot A) \quad \text{(Equation 10)}$$

The embodiments of the disclosure that are described using $PM_{2.5}$ pollutant particles with a box model are only for a better understanding of the embodiments described herein. Thus, those embodiments do not adversely limit the scope of the disclosure. For example, any appropriate model for the monitored area, modification to the above equations, or a different set of equations, to estimate the pollution contribution caused by the monitored area, can be used. To simplify the illustration, those approaches will not be discussed.

The embodiments of the disclosure may be a system, a method, and/or a computer program product with any technically detailed level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer implemented method of monitoring air pollution over an area, the method comprising the steps of:
    obtaining, by one or more processing units, a location data from sensors at stations that are deployed along a boundary of a monitored area, wherein a number of the stations deployed along the boundary of the monitored area is based on a size and type of the monitored area as well as a number of moving emission sources within the monitored area, wherein the moving emission sources move throughout the monitored area;
    obtaining, by one or more processing units, an air pollution data from the sensors;
    obtaining, by one or more processing units, a macroscale atmospheric data of a region that the monitored area belongs to;
    estimating, by one or more processing units, a boundary pollutant distribution based on the obtained location data and air pollution data, wherein the boundary pollutant distribution is a measure of distribution of pollutant along the boundary of the monitored area;
    estimating, by one or more processing units, a horizontal diffusion and a vertical diffusion of the monitored area, based on the boundary pollutant distribution and the macroscale atmospheric data; and
    calculating, by one or more processing units, a pollution contribution caused by the monitored area based on the estimated the boundary pollutant distribution, the estimated horizontal diffusion, and the vertical diffusion by utilizing a box model, wherein a height of the box model correlates with another height of an atmospheric surface layer within the monitored area.

2. The method of claim 1, wherein the estimation of the boundary pollutant distribution comprises:
    utilizing an interpolation algorithm to estimate the boundary pollutant distribution along the boundary of the monitored area.

3. The method of claim 1 further comprising:
    estimating, by one or more processing units, a pollutant concentration of the monitored area based on the boundary pollutant distribution.

4. The method of claim 3, wherein the estimation of the horizontal diffusion and vertical diffusion of the monitored area comprises:
    estimating, by one or more processing units, parameters of a surface wind and a vertical wind that are within the monitored area and based on the macroscale atmospheric data; and
    decreasing, by one or more processing units, an error of the parameters of the surface wind and the vertical wind by fusing the macroscale atmospheric data and the air pollution data.

5. The method of claim 4, wherein the estimation of the horizontal diffusion and vertical diffusion of the monitored area comprises the step of:
    estimating, by one or more processing units, the horizontal diffusion and the vertical diffusion are based on the pollutant concentration and the parameters of the surface wind and the vertical wind.

6. The method of claim 5, wherein the calculation of the pollution contribution further comprising:
    calculating, by one or more processing units, a change rate of the pollutant concentration of the monitored area based on the pollutant concentration; and calibrating, by one or more processing units, the change rate of the pollutant concentration based on the horizontal diffusion and the vertical diffusion.

7. The method of claim 6, wherein the calculation of the pollution contribution comprises the step of:
calculating, by one or more processing units, the pollution contribution based on the calibrated change rate of the pollutant concentration and a volume of the monitored area.

8. The method of claim 2, wherein the estimation of the boundary pollutant distribution further comprising:
determining, by one or more processing units, the boundary pollutant distribution with minimized error by adopting h/(n-h) cross validation, wherein 0<h<n/2, and h is a natural number, n is the number of the stations.

9. A computer system of monitoring air pollution over an area, comprising:
a processor;
a computer-readable memory coupled to the processor, the memory comprising instructions that when executed by the processor perform actions of:
obtaining location and air pollution data from sensors at stations positioned along a boundary of monitored area along with macroscale atmospheric data of a region that the monitored area belongs to, wherein a number of the stations deployed along the boundary of the monitored area is based on a size and type of the monitored area as well as a number of moving emission sources within the monitored area, wherein the moving emission sources move throughout the monitored area;
estimating a boundary pollutant distribution based on the location data and the air pollution data, wherein the boundary pollutant distribution is a measure of distribution of pollutant along the boundary of the monitored area;
estimating a horizontal diffusion and a vertical diffusion of the monitored area that is based on the boundary pollutant distribution and the macroscale atmospheric data; and
calculating a pollution contribution caused by the monitored area that is based on the boundary pollutant distribution, the horizontal diffusion, and the vertical diffusion by utilizing a box model, wherein a height of the box model correlates with another height of an atmospheric surface layer within the monitored area.

10. The system of claim 9, wherein the estimation of the boundary pollutant distribution which comprises:
utilizing an interpolation algorithm to estimate the boundary pollutant distribution along the boundary of the monitored area.

11. The system of claim 9 further comprising:
estimating a pollutant concentration of the monitored area that is based on the boundary pollutant distribution.

12. The system of claim 11, wherein the estimating horizontal diffusion and vertical diffusion of the monitored area comprises:
estimating parameters of a surface wind and a vertical wind in the monitored area that is based on the macroscale atmospheric data; and
decreasing an error of the surface wind and the vertical wind parameters by fusing the macroscale atmospheric data and the air pollution data.

13. The system of claim 12, wherein the estimating horizontal diffusion and vertical diffusion of the monitored area comprises:
estimating the horizontal diffusion and the vertical diffusion based on the pollutant concentration and the parameters of the surface wind and the vertical wind.

14. The system of claim 13, wherein the calculating pollution contribution further comprises:
calculating a change rate of the pollutant concentration in the monitored area based on the pollutant concentration; and
calibrating the change rate of the pollutant concentration based on the horizontal diffusion and the vertical diffusion.

15. The system of claim 14, wherein the calculating pollution contribution further comprises:
calculating a pollution contribution based on the calibrated change rate of the pollutant concentration and the volume of the monitored area.

16. A computer readable storage medium having computer readable instructions that when executed by a least one computer cause the computer to:
obtain a location data and an air pollution data from sensors at stations positioned along a boundary of a monitored area, along with a macroscale atmospheric data of a region that the monitored area belongs to, wherein a number of the stations deployed along the boundary of the monitored area is based on a size and type of the monitored area as well as a number of moving emission sources within the monitored area, wherein the moving emission sources move throughout the monitored area;
estimate a boundary pollutant distribution based on the location data and the air pollution data, wherein the boundary pollutant distribution is a measure of distribution of pollutant along the boundary of the monitored area;
estimate a horizontal diffusion and a vertical diffusion of the monitored area based on the boundary pollutant distribution and the macroscale atmospheric data; and
calculate a pollution contribution caused by the monitored area based on the boundary pollutant distribution, the horizontal diffusion, and the vertical diffusion by utilizing a box model, wherein a height of the box model correlates with another height of an atmospheric surface layer within the monitored area.

17. The computer readable storage medium of claim 16, wherein the estimation of the boundary pollutant distribution comprises the instruction to:
utilize an interpolation algorithm to estimate the boundary pollutant distribution along the boundary of the monitored area.

18. The computer readable storage medium of claim 16, wherein the program instructions executable by a processor to cause the processor to:
estimate a pollutant concentration of the monitored area based on the boundary pollutant distribution.

* * * * *